United States Patent [19]

Rossi et al.

[11] Patent Number: 5,272,262
[45] Date of Patent: Dec. 21, 1993

[54] METHOD FOR THE PRODUCTION OF CATALYTIC RNA IN BACTERIA

[75] Inventors: John J. Rossi, Glendora; Nerida Taylor, Loma Linda, both of Calif.

[73] Assignee: City of Hope, Duarte, Calif.

[21] Appl. No.: 854,598

[22] PCT Filed: Oct. 19, 1990

[86] PCT No.: PCT/US90/06032
§ 371 Date: Jun. 9, 1992
§ 102(e) Date: Jun. 9, 1992

Related U.S. Application Data

[63] Continuation-in-part of Ser. No. 369,489, Jun. 21, 1989, Pat. No. 5,144,029, and a continuation-in-part of Ser. No. 401,613, Aug. 31, 1989, abandoned.

[51] Int. Cl.⁵ .................. C07H 15/12; C12Q 1/68; C12P 21/06; C12P 21/02
[52] U.S. Cl. .................. 536/23.2; 435/6; 435/69.1; 435/70.3; 435/71.2; 435/91.31; 435/172.1; 435/172.3; 435/252.3; 435/252.33
[58] Field of Search .................. 536/23.1, 23.2; 435/6, 435/69.1, 76.3, 71.2, 91, 172.1, 172.3, 252.3, 252.13

[56] References Cited

PUBLICATIONS

Chem. Abst. 110 (21):187321k, 1988.
Chem. Abst. 112(7):51284j 1989.
M. Baer, et al. Science, 228:999–1002, 1985.
Cameron et al., PNAS 86:9139–9143.

*Primary Examiner*—John W. Rollins
*Attorney, Agent, or Firm*—Edward S. Irons

[57] ABSTRACT

*E. coli* transformed with genes which express anti-HIV-1 ribozymes. Mammalian cells which express HIV-1 gag ribozymes.

11 Claims, 5 Drawing Sheets

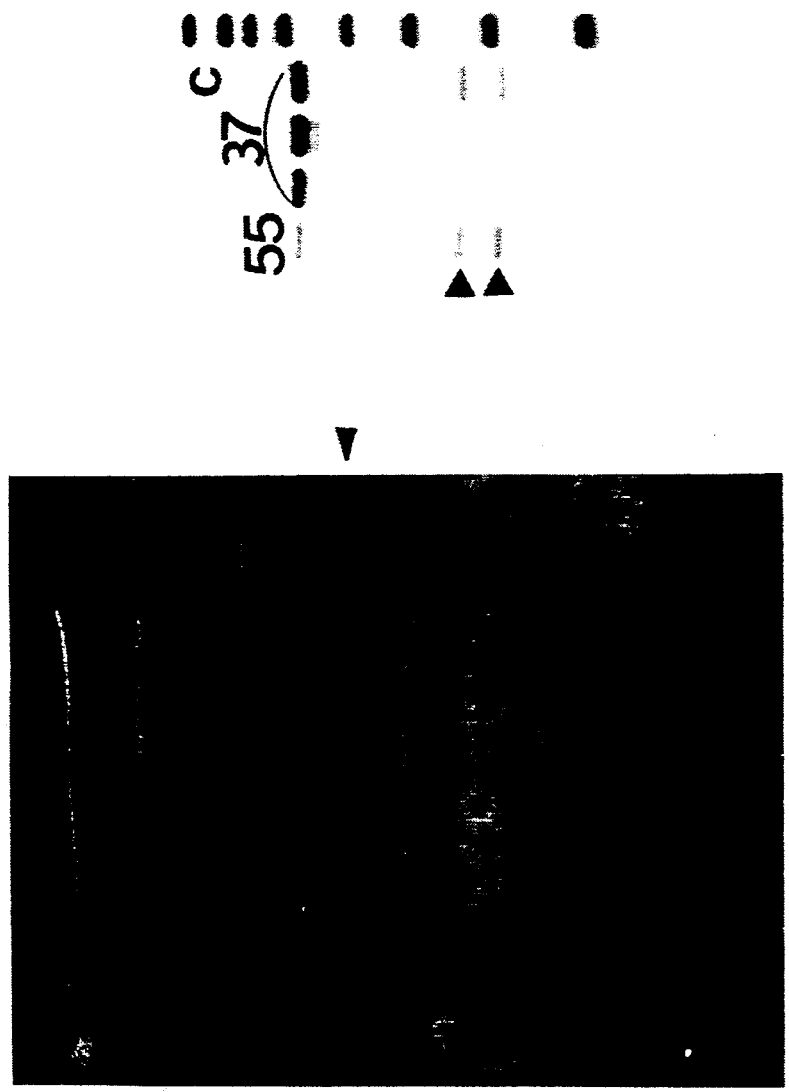
FIG. 7
FIG. 5
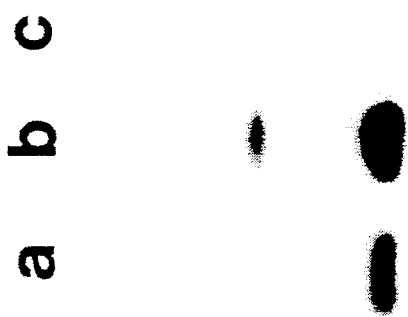
FIG. 3

METHOD FOR THE PRODUCTION OF CATALYTIC RNA IN BACTERIA

This invention was made with government support under Grant No. J.R. NIAID R01 AI29329 awarded by the National Institutes of Health. The government has certain rights in the invention.

This application is a continuation-in-part of Rossi, Cantin, Zaia and Chang U.S. application Ser. No. 07/369,489 filed 21 Jun. 1989, now U.S. Pat. No. 5,144,019, and of Rossi, Cantin, Zaia and Chang U.S. application Ser. No. 07/401,613 filed 31 Aug. 1989, now abandoned as a continuation-in-part of Ser. No. 07/369,489. Application Ser. No. 07/369,489 and application Ser. No. 07/401,613 are incorporated herein by reference.

This invention relates to a method for the production of catalytic RNA (ribozymes) in cells, including mammalian and bacterial cells. More particularly, the invention relates to synthetic genes which encode a ribozyme, to mammalian and bacterial cells having such genes transformed therein, and to the ribozyme containing expression products of such bacteria. The invention also includes the in vitro and therapeutic use of such expression products.

BACKGROUND OF THE INVENTION

One form of gene expression impairment by RNA-RNA duplex formation has been termed "antisense" inhibition. Exploitation of antisense gene regulation could lead to potent anti-viral therapy. A serious limitation of the antisense approach, especially as it applies to anti-viral activity, is that it is stoichiometric and may require large molar excesses of anti-sense versus target RNA to be effective.

Within recent years, discoveries of ribozymes, e.g., RNAs with enzymatic activities have led to the development of antisense molecules which not only form RNA-RNA hybrids, but catalytically cleave the covalent phosphodiester linkages and turn over large numbers of substrate molecules. Ribozymes can now be targeted to virtually any RNA transcript, and efficient cleavage can be readily achieved in vitro. See, Kim, S. H., et al. *Proc. Natl Acad. Sci. U.S.A.* 84:8788–8792 (1987); Haseloff, J., et al., *Nature* 234:585–591 (1988); PCT published application WO/89/05852; Cech, T.R. *JAMA* 260:3030–3034 (1988); PCT published application WO/88/04300; Jeffries, A. G., et al., *Nucleic Acids Research* 17:1371–1377 (1989).

U.S. Pat. No. 5,144,019 and application Ser. No. 401,613 describe stable, catalytically efficient ribozymes useful, inter alia, to cleave HIV-1 RNA or any other viral or endogenous cellular RNA in vitro and in vivo, mammalian cells transformed with such ribozymes, vectors useful to accomplish such transformation and the use for human therapy of such ribozymes whether produced synthetically or as expressed by such transformed cells. See Chang, et al. *Clinical Biotechnology* 2:23–31 (1990) which is incorporated herein by reference.

SUMMARY OF THE INVENTION

The production of large amounts of specifically targeted ribozymes for therapeutic use is problematical. This invention provides a novel method for the large scale production of any ribozyme by expression of a stable RNA molecule into which catalytic RNA has been inserted. Any stable RNA can be utilized. In the preferred practice of the invention, *E. Coli* is transformed by Tac promoter driven 4.5 S RNA having a catalytic RNA sequence inserted therein. High levels of expression of such fusion RNAs can be achieved by varying the temperature of growth, using mutants of *E. Coli* or other bacteria which are defective in certain enzymatic activities such as RNAse III, inducing expression with isopropyl thio $\beta$ galactopyranoside (IPTG) in an appropriate host, preparing a set of nested deletions within the 4.5 S or similar gene to eliminate undesirable folding and by other standard molecular biological techniques.

The invention also includes synthetic genes which encode catalytic RNA, microorganisms transformed with such genes, the catalytic RNA containing expression products of such genes and the in vitro and therapeutic use of such expression products.

DESCRIPTION OF THE FIGURES

FIG. 3 is a Northern analysis showing the expression of an anti-HIV-1 gag ribozyme fused with 4.5 S RNA (lanes a and b) and 4.5 S RNA alone (lane c).

FIG. 5 depicts a preparative gel including ethidium stained RNAs as shown by FIG. 4. The arrowhead points to the fusion ribozymes.

FIG. 7 depicts a gel electrophoresis analysis demonstrating in vitro cleavage reactions using the *E. Coli* transformants produced by 4.5 S fusion ribozymes.

DETAILED DESCRIPTION OF THE INVENTION

Heretofore, the preferred way to make ribozymes for in vitro studies or delivery to cells in culture was to scale up an in vitro transcription reaction. This invention eliminates the need for in vitro transcription thus greatly reducing the cost of producing large quantities of ribozyme.

In its more generic embodiments, the invention provides a novel method for the large scale production of any ribozyme by the expression of a stable bacterial RNA molecule into which a ribozyme sequence has been inserted.

The stable RNA can be any RNA and the insert can be any ribozyme. More specifically, any small stable bacterial RNA for which a gene is available may be utilized. The RNA molecule is preferably small, i.e., contains from about 50 to 200 nucleotides and is preferably an *E. Coli* RNA. *E. Coli* 4.5 S RNA is used in the method presently deemed to be the best mode for the practice of the invention.

Among others, any of the ribozymes described in U.S. Pat. No. 5,144,109 or Ser. No. 401,613 may be used. A strong prokaryotic promoter system is chosen to facilitate overproduction of the RNA-ribozyme fusion product. Vectors including the stable RNA, ribozyme and promoter are transformed into bacteria selected to abundantly produce such fusion products.

In general, consensus sequence promoters are useful in the practice of this invention. The Tac promoter system is preferred. The thermally inducible lambda pL promoter system may also be utilized.

Vectors comprising, in combination, a stable RNA, an inserted ribozyme, and an appropriate promoter and a transcriptional terminator are an important component of the invention. Such vectors are constructed and transformed into bacteria in known manner.

EXAMPLE I

Figure 1:
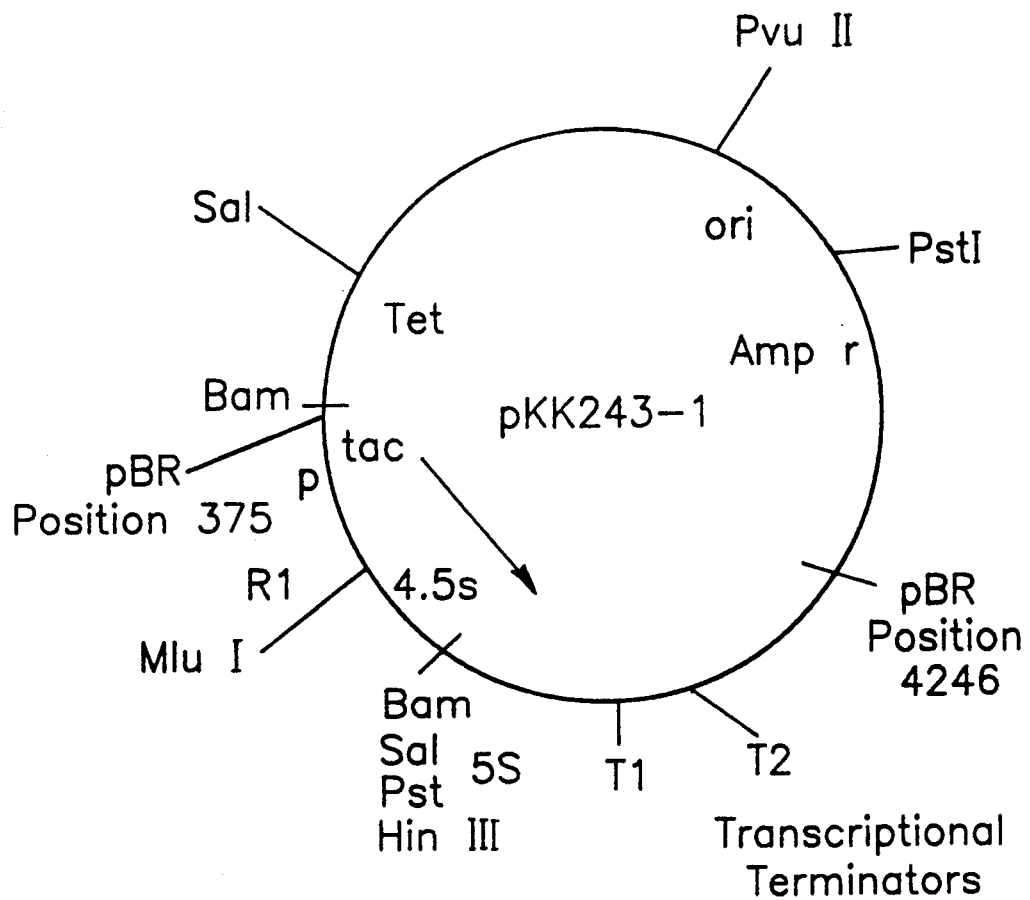
FIG. 1 illustrates a vector containing a Tac promoter and a ribozyme fused to an *E. Coli* 4.5 S RNA gene.
Figure 2:
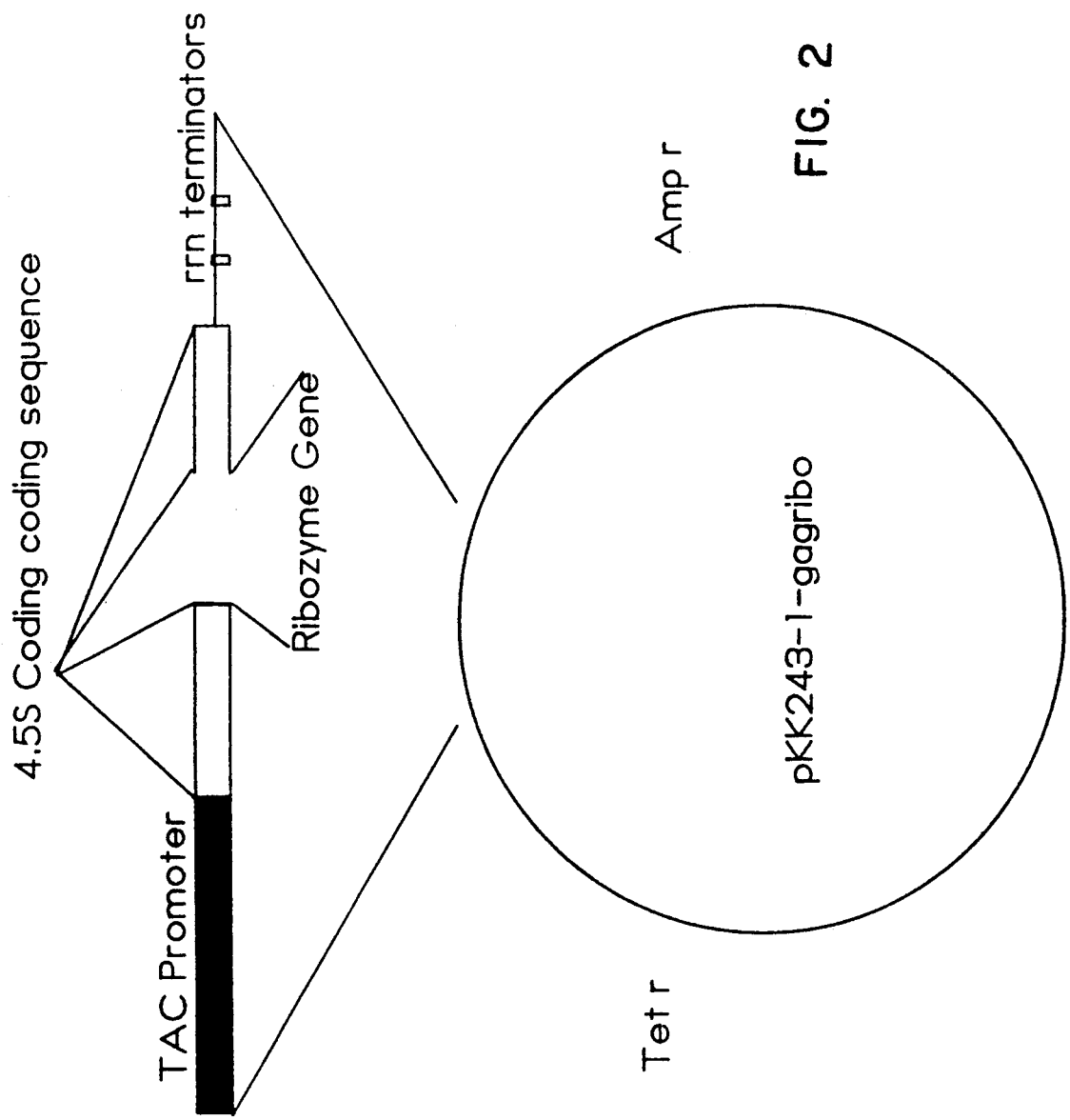
FIG. 2 illustrates the vector shown by FIG. 1 with the transcriptional unit containing the ribozyme depicted by FIG. 1.

The $E.$ $Coli$ 4.5 S RNA gene is described in the prior art. See Brosius, J., et al., $Biological$ $Chemistry$ 260:3539-3541 (1985). This gene includes an MluI restriction site. The anti-HIV-1 gag ribozyme gene having the sequence 5' GGATCCGCTTAATACTCTGATGAGTCCGTGAGGACGAAACGCT CTCGCACCGGATCC 3' is inserted into the MluI site of the 4.5 S RNA molecule to produce the FIG. 1 construct in the following manner:

The plasmid pKK243-1 was cut at the unique MluI restriction sight in the 4.5 S gene sequence. The staggered ends created by this digestion were filled in by Klenow DNA polymerase and dephosphorylated with calf intestine phosphatase. Two synthetic DNA oligomers with 10 bases of complementary sequences at their 3' termini, GAGHAM 1(GGCCGGATCCGCTTAATACTCTGATGAGTCCGTGAGGAC) and 2(CCGGATCCGCGAGAGCGTTTCGTCCTCACGG), were polymerized into a double stranded fragment with Taq polymerase by mixing equimolar amounts together in a 50 μliter reaction containing ca. 0.5 μgms of each oligo, 125 μmoles each dNTP, Taq polymerase buffer (Cetus-Perkin Elmer) and 2.5 units of Taq polymerase.

A series of 10 amplification cycles was carried out using the following: 94C-1 min., 37C-1 min. and 72C-2 min. The polymerized fragment was phosphorylated, ligated with pKK243-1 vector and transformed into $E.$ $Coli$ strain MC 1061 by standard calcium chloride techniques. Transformants were screened for the ribozyme insert and clones harboring the insert were examined for expression using a Northern gel analysis (see FIG. 3). Low molecular weight RNA was harvested from positive clones by the following method. Cells were suspended in cold 50 Mm Tris pH 7.5, 5 mM $MgCl_2$ and acid phenol extracted twice made to 0.3M NaOAc pH 5.5 and precipitated with 3.5 volumes of ethanol. The pellet was washed with 70% ethanol and resuspended in sterile water. Aliquots of this RNA were run on a 6% acrylamide (20:1 acrylamide:bis) gel at 40 millamps in TBE buffer, transferred to Zeta Probe nylon filter by electroblotting at 90 mamps overnight, and hybridized with radioactively labeled gag ribozymes specific probe GAGRAM 2. Such Northern analysis showed both precursor (lane c) and final products (lanes a and b, FIG. 3). The clone with the highest expression was chosen for further study. Both the precursor and processed product were cultured in "L" broth at 37° C. and monitored for ribozyme activity after they were purified by overnight diffusion elution from the acrylamide gel in 0.3M NaOAc pH 5.5, 0.1% SDS. Following elution, the RNA was extracted 2 times with phenol, once with dichloromethane, ethanol precipitated, pelleted by centrifugation and washed with 70% ethanol. The RNA was dissolved in water before use. RNA fragments were tested for in vitro cleavage activity by the methods described by Chang, et al., supra.

Figure 4:
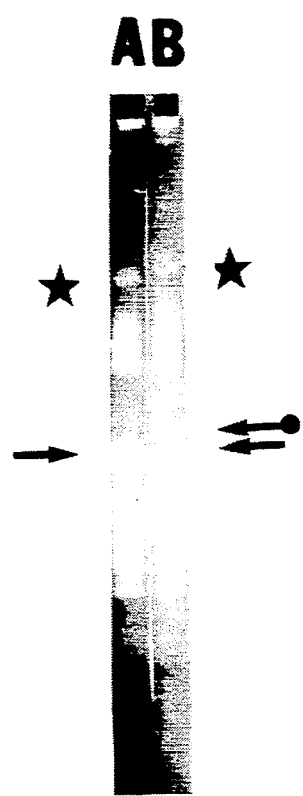
FIG. 4 depicts an ethidium bromide stained gel of an acid-phenol extract of small RNAs overproduced by *E. Coli* transformants in accordance with the invention.
Figure 6:
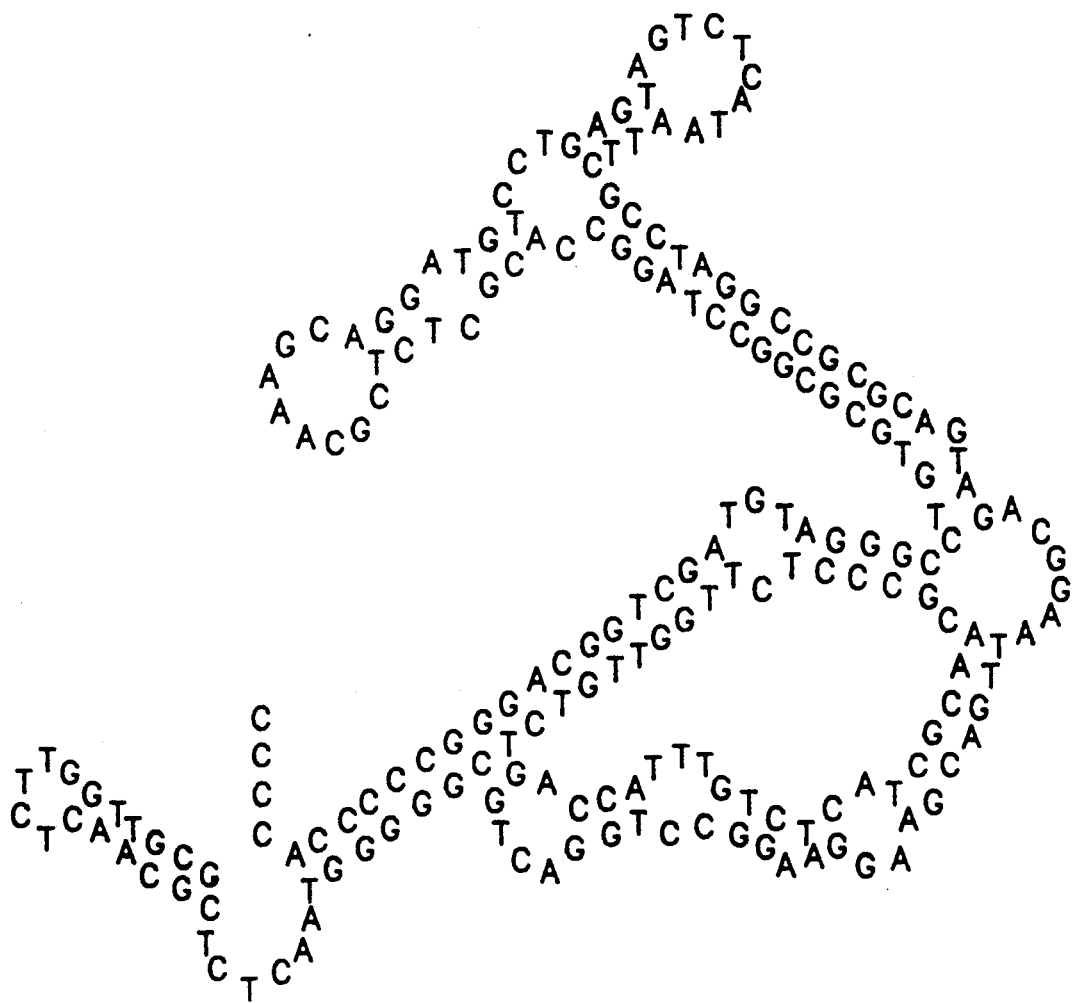
FIG. 6 is a composite depiction of the RNA folding of the ribozyme embedded in the 4.5 S transcript.

FIG. 4 depicts an ethidium bromide stained gel of an acid-phenol extract of small RNAs by which 4.5 S (left lane) and 4.5 S with an 8 bp insertion on the MluI site (right lane) which were overproduced by such transformants. The arrows indicate the ethidium bromide stained products (4.5 S) (4.5 S and 8 pb insertion) derived from less than 1 ml of cell culture.

FIG. 5 depicts a preparative acid-phenol extract of RNA from approximately 250 mls of cell. The arrow points to the 4.5 S gag ribozyme fusion transcript. This transcript was excised from the gel and shown to be catalytically functional (see FIG. 7).

What is claimed is:

1. The vector depicted by FIG. 1.

2. A mammalian or a bacterial cell transformed with a synthetic gene which encodes catalytic RNA or with the vector defined by claim 1.

3. A bacterial cell transformed with a synthetic gene which encodes catalytic RNA or with the vector defined by claim 1.

4. A vector as defined by claim 1 in which said ribozyme is an anti-HIV-1 gag ribozyme.

5. A vector as defined by claim 4 in which the anti-HIV-1 gag ribozyme gene has the sequence 5' GGATCCGCTTAATACTCTGATGAGTCCGTGAGGACGAAACGCT GCACCGGATCC 3'.

6. The expression product of a cell transformed with a vector comprising a Tac promoter and a ribozyme fused to an $E.$ $Coli$ 4.5 S RNA gene.

7. The expression product of claim 6 in which said cell is a bacterial cell.

8. The expression product as defined by claim 7 in which said bacterial cell is an $E.$ $Coli$ cell.

9. The expression product as defined by claim 7 or claim 8 in which said ribozyme is an anti-HIV-1 gag ribozyme.

10. The expression product as defined by claim 7 or claim 8 in which said ribozyme comprises the sequence 5' GGAUCCGCUUAAUACUCUGAUGAGUCCGUGAGGACGAAACGCU CUCGCACCGGAUCCGCGUGUGCC 3'.

11. The method which comprises cleaving HIV-1 RNA by reaction with an expression product as defined by claim 7 or claim 8.

* * * * *